US00PP19222P2

(12) United States Plant Patent
Miedema-Jorna

(10) Patent No.: US PP19,222 P2
(45) Date of Patent: Sep. 16, 2008

(54) **NEW GUINEA *IMPATIENS* PLANT NAMED 'TAMAR SHOCKING PINK'**

(50) Latin Name: *Impatiens hawkeri*
Varietal Denomination: Tamar Shocking Pink

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/974,210

(22) Filed: Oct. 11, 2007

(51) Int. Cl.
*A01H 5/00* (2006.01)

(52) U.S. Cl. ..... Plt./318.5

(58) Field of Classification Search ..... Plt./318.5
See application file for complete search history.

*Primary Examiner*—Annette H Para
(74) *Attorney, Agent, or Firm*—C. A. Whealy

(57) ABSTRACT

A new and distinct cultivar of *Impatiens* plant named 'Tamar Shocking Pink', characterized by its upright and outwardly spreading growth habit; mounded plant form; freely branching habit; dark green-colored leaves; freely flowering habit; large dark pink-colored flowers; and good garden performance.

1 Drawing Sheet

Botanical designation: *Impatiens hawkeri.*
Cultivar denomination: 'Tamar Shocking Pink'.

BACKGROUND OF THE INVENTION

The present invention relates to a new and distinct cultivar of New Guinea *Impatiens,* botanically known as *Impatiens hawkeri* and hereinafter referred to by the name 'Tamar Shocking Pink'.

The new *Impatiens* is a product of a planned breeding program conducted by the Inventor in De Lier, The Netherlands. The objective of the breeding program is to create new freely-branching New Guinea *Impatiens* cultivars with freely flowering habit and large attractive flowers.

The new *Impatiens* originated from a cross-pollination made by the Inventor in De Lier, The Netherlands of a proprietary selection of *Impatiens hawkeri* identified as code number AM1 071040, not patented, as the female, or seed, parent with a proprietary selection of *Impatiens hawkeri* identified as code number AM1 071050, not patented, as the male, or pollen, parent. The new *Impatiens* was discovered and selected by the Inventor as a single flowering plant within the progeny of the stated cross-pollination in a controlled environment in De Lier, The Netherlands in 2003.

Asexual reproduction of the new *Impatiens* by terminal cuttings in a controlled environment in De Lier, The Netherlands since 2004, has shown that the unique features of this new *Impatiens* are stable and reproduced true to type in successive generations.

SUMMARY OF THE INVENTION

The cultivar Tamar Shocking Pink has not been observed under all possible environmental conditions. The phenotype may vary somewhat with variations in environment and cultural practices such as temperature and light intensity, without, however, any variance in genotype.

The following traits have been repeatedly observed and are determined to be the unique characteristics of 'Tamar Shocking Pink'. These characteristics in combination distinguish 'Tamar Shocking Pink' as a new and distinct cultivar of *Impatiens:*

1. Upright and outwardly spreading growth habit; mounded plant form.
2. Freely branching habit.
3. Dark green-colored leaves.
4. Freely flowering habit.
5. Large dark pink-colored flowers.
6. Good garden performance.

Plants of the new *Impatiens* can be compared to plants of the female parent selection. Plants of the new *Impatiens* differ from plants of the female parent selection in the following characteristics:

1. Plants of the new *Impatiens* are more vigorous than plants of the female parent selection.
2. Plants of the new *Impatiens* have lighter-colored leaves than plants of the female parent selection.

Plants of the new *Impatiens* can be compared to plants of the male parent selection. Plants of the new *Impatiens* differ from plants of the male parent selection in the following characteristics:

1. Plants of the new *Impatiens* are less vigorous than plants of the male parent selection.
2. Plants of the new *Impatiens* have narrower leaves than plants of the male parent selection.

Plants of the new *Impatiens* can be compared to plants of the *Impatiens* cultivar Paradise Parita, not patented. In side-by-side comparisons conducted in De Lier, The Netherlands, plants of the new *Impatiens* differed from plants of the cultivar Paradise Parita in the following characteristics:

1. Plants of the new *Impatiens* had smaller leaves than plants of the cultivar Paradise Parita.
2. Plants of the new *Impatiens* had smaller flowers than plants of the cultivar Paradise Parita.
3. Plants of the new *Impatiens* had darker pink-colored flowers than plants of the cultivar Paradise Parita.

BRIEF DESCRIPTION OF THE PHOTOGRAPH

The accompanying colored photograph illustrates the overall appearance of the new *Impatiens,* showing the colors as true as it is reasonably possible to obtain in colored reproductions of this type. Colors in the photograph may differ slightly from the color values cited in the detailed botanical description which accurately describe the colors of the new *Impatiens*. The photograph comprises a top perspective view of a typical flowering plant of 'Tamar Shocking Pink' grown in a container.

DETAILED BOTANICAL DESCRIPTION

The aforementioned photographs and following observations, measurements and values describe plants grown in De Lier, The Netherlands, in 12-cm containers and under commercial practice during the autumn in a glass-covered greenhouse with day and night temperatures averaging 18° C. Rooted young plants had been growing for about three months when the photograph and description were taken. In the following description, color references are made to The Royal Horticultural Society Colour Chart, 1995 Edition, except where general terms of ordinary dictionary significance are used.

Botanical classification: *Impatiens hawkeri* cultivar Tamar Shocking Pink.

Parentage:

*Female, or seed, parent.*—Proprietary selection of *Impatiens hawkeri* identified as code number AM1 071040, not patented.

*Male, or pollen, parent.*—Proprietary selection of *Impatiens hawkeri* identified as code number AM1 071050, not patented.

Propagation:

*Type.*—By terminal cuttings.

*Time to initiate roots, summer.*—About five to seven days at temperature of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About 14 to 21 days at temperatures of 19° C. to 20° C.

*Root description.*—Fine; white to brown in color.

*Rooting habit.*—Freely branching.

Plant description:

*Plant and growth habit.*—Upright and outwardly spreading growth habit; mounded plant form. Freely branching habit with about four lateral branches; pinching is typically not required. Moderately vigorous growth habit.

*Plant height.*—About 25 cm.

*Plant diameter.*—About 35 cm.

Lateral branch description:

*Length.*—About 21 cm.

*Diameter.*—About 1.4 cm.

*Internode length.*—About 5 cm.

*Strength.*—Moderately strong.

*Aspect.*—Initially upright to outwardly spreading.

*Texture.*—Smooth, glabrous; slightly glossy in luster.

*Color.*—175A.

Foliage description:

*Arrangement.*—Opposite or in whorls of about five; simple.

*Length.*—About 12.5 cm.

*Width.*—About 3.7 cm.

*Shape.*—Elliptic.

*Apex.*—Acute.

*Base.*—Attenuate.

*Margin.*—Serrate with ciliation.

*Texture, upper and lower surfaces.*—Smooth, glabrous; leathery; moderately glossy in luster.

*Venation pattern.*—Pinnate; arcuate.

*Color.*—Developing foliage, upper surface: Darker than 137A. Developing foliage, lower surface: 138B. Fully expanded foliage, upper surface: 139A; venation, 182B. Fully expanded foliage, lower surface: 138B; venation, 183C.

*Petiole.*—Length: About 3.2 cm. Diameter: About 4 mm. Texture, upper and lower surfaces: Smooth, glabrous. Color, upper surface: 183C. Color, lower surface: 184B.

Flower description:

*Flower type and flowering habit.*—Single rounded axillary flowers. Freely flowering habit; usually about twenty flowers develop per lateral branch. Flowers positioned above the foliage and typically face upright or outward. Flowers last about ten days on the plant under greenhouse conditions. Petals self-cleaning, gynoecium persistent. Flowers not fragrant.

*Natural flowering season.*—Year-round under greenhouse conditions. In the garden, flowering from spring through summer in The Netherlands. Plants begin flowering about nine weeks after planting.

*Flower size.*—Diameter: About 6 cm. Depth: About 1.1 cm.

*Flower buds.*—Length: About 1.2 cm. Diameter: About 8 mm. Shape: Ovoid; pointed. Color: 52A.

*Petals.*—Quantity/arrangement: Five per flower in a single whorl. Length, banner petal: About 2.5 cm. Length, lateral and lower petals: About 2.8 cm. Width, banner petal: About 5 cm. Width, lateral and lower petals: About 2.8 cm. Shape, all petals: Broadly cordate. Apex, all petals: Deeply emarginate. Base, all petals: Acute. Margin, all petals: Entire. Texture, all petals, upper and lower surfaces: Smooth, glabrous. Color, banner petal: When opening and fully opened, upper surface: 52B; towards the margins, 52C; center, 52A and 52D. When opening and fully opened, lower surface: 52B; towards the margins, 52C. Color, lateral and lower petals: When opening and fully opened, upper surface: 52B; towards the margins, 52C; center, 52A and 52D. When opening and fully opened, lower surface: 52B to 52C.

*Sepals.*—Quantity/arrangement: Three; one modified into an elongated spur. Length, spurred sepal: About 1.6 cm. Length, lateral sepals: About 1.2 cm. Width, spurred sepal: About 2.1 cm. Width, lateral sepals: About 6 mm. Shape, spurred sepal: Broadly ovate. Shape, lateral sepals: Ovate. Apex, all sepals: Apiculate. Base, all sepals: Cuneate. Margin, all sepals: Entire. Texture, all sepals, upper and lower surfaces: Smooth, glabrous. Color, spurred sepal: Immature, upper surface: Between 55D and 52C; towards the apex, 144A. Immature, lower surface: Between 55D and 52A; towards the apex, 144A. Mature, upper surface: Between 55B and 55D; towards the apex, 144A. Mature, lower surface: Between 55C to 55D and 52A. Color, lateral sepals: Immature, upper surface: Between 55D and 52C; towards the apex, 144A. Immature, lower surface: Between 55D and 52A; towards the apex, 144A. Mature, upper and lower surfaces: Between 52A and 55D. Spur length: About 4.6 cm. Spur diameter: At flower, about 2 mm;

at apex, less than 1 mm. Spur texture: Smooth, glabrous. Spur color: 53B.

*Peduncles.*—Length: About 6.8 cm. Diameter: About 2 mm. Angle: About 45° from vertical. Strength: Moderately strong. Texture: Smooth, glabrous. Color: Between 177B and 180A.

*Reproductive organs.*—Stamens: Quantity: Five fused at anthers; filaments free. Anther length: About 2 mm. Anther color: 55C tinted with 155D. Pollen amount: Scarce. Pollen color: 158D. Pistils: Quantity per flower: One. Pistil length: About 1 mm. Stigma shape: Rounded. Stigma color: 158C. Ovary color: 144A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Tamar Shocking Pink' as illustrated and described.

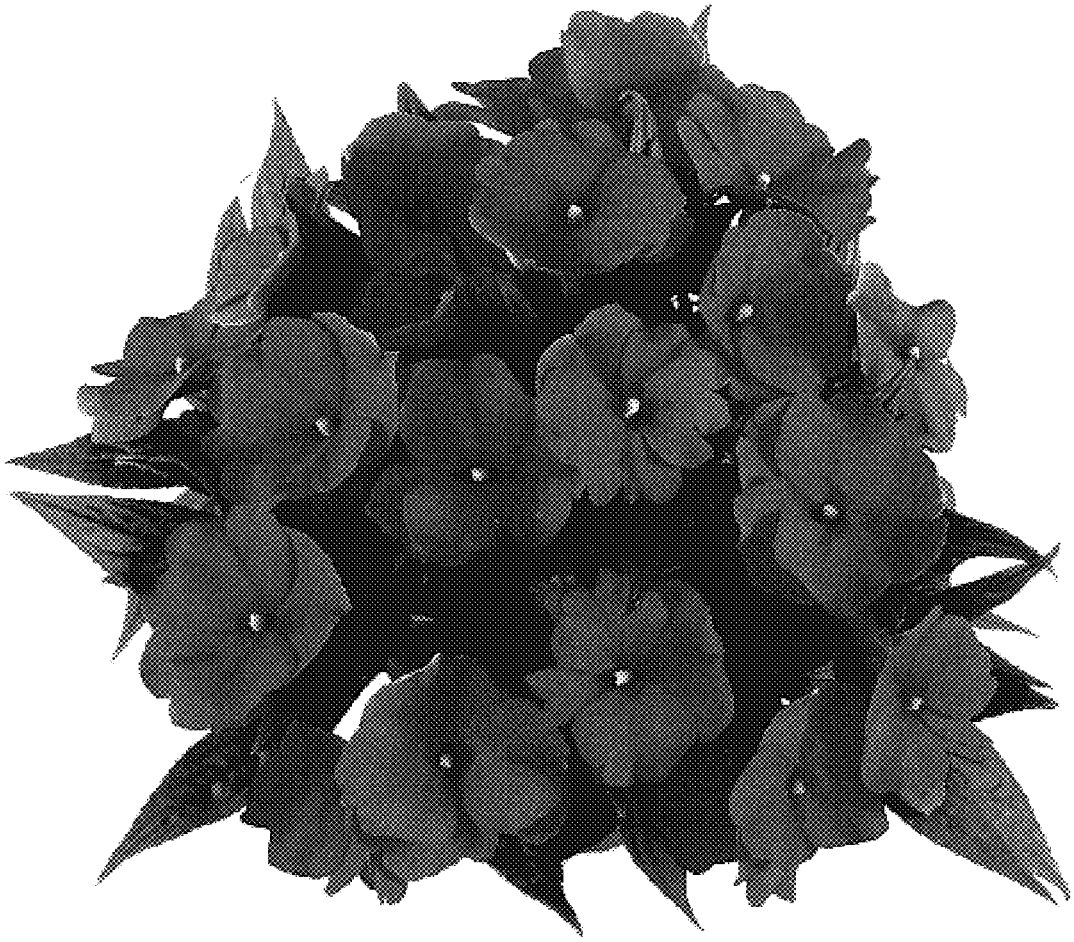

* * * * *